(12) United States Patent
Morken et al.

(10) Patent No.: US 6,242,262 B1
(45) Date of Patent: *Jun. 5, 2001

(54) METHOD AND APPARATUS FOR SCREENING CATALYST LIBRARIES

(75) Inventors: James P. Morken, Chapel Hill; Steven J. Taylor, Carrboro, both of NC (US)

(73) Assignee: The University of North Carolina at Chapel Hill, Chapel Hill, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/957,191

(22) Filed: Oct. 24, 1997

(51) Int. Cl.$^7$ .......................... G01N 31/10; G01N 25/20; G01N 33/543; G01N 33/53

(52) U.S. Cl. .......................... 436/37; 436/147; 436/159; 436/518; 436/523; 436/524; 436/525; 436/526; 436/527; 436/528; 436/529; 436/530; 436/531; 436/532; 435/DIG. 14; 435/DIG. 21

(58) Field of Search .......................... 436/518, 523–531, 436/37, 147, 159; 435/DIG. 14, DIG. 21

(56) References Cited

U.S. PATENT DOCUMENTS

| | | | |
|---|---|---|---|
| 5,565,324 | 10/1996 | Still et al. | 435/6 |
| 5,876,946 | 3/1999 | Burbaum et al. | 435/7.1 |
| 6,030,917 | * 2/2000 | Weinberg et al. | |
| 6,063,633 | * 5/2000 | Wilson, III | |

OTHER PUBLICATIONS

Gilbertson et al. The Combinatorial Synthesis of Chiral Phosphine Ligands. Tetrahedron Letters 37(36): 6475–6478, 1996.*

Gallop et al. Applications of Combinatorial Technologies to Drug Discovery. 1. J. Med. Chem. 37(9): 1233–1251, 1994.*

F. M. menger et al. J. Org. Chem, vol. 60, pp 6666–6667, 1995.*

Brenner et al. PNAS USA 89:5381, 1992.*

Ohlmeyer et al.; Complex synthetic chemical libraries indexed with molecular tags, *Proc. Natl. Acad. Sci, USA*, 90:10922–10926 (1993).

Melamed et al.; An Historical Review of the Development of Flow Cytometers and Sorters, *Flow Cytometry and Sorting*, Second Edition:1–9 (1990).

Moates et al.; Infrared Thermographic Screening of Combinatorial Libraries of Heterogeneous Catalysts, *Ind. Eng. Chem. Res*, 35:4801–4803 (1996).

* cited by examiner

Primary Examiner—Jyothsna Venkat
Assistant Examiner—Maurie E. Garcia
(74) Attorney, Agent, or Firm—Myers Bigel Sibley & Sajovec

(57) ABSTRACT

A method for isolating an active catalyst from a library of compounds that are potential catalysts is disclosed. The method involves providing a library which comprises a plurality of discrete solid supports, each solid support having a different organic compound bound thereto; and providing a reaction solution in a reaction vessel, the reaction solution containing the reactant or reactants necessary for a chemical reaction to occur in the presence of a catalyst for that reaction. The library and the reaction solution are then combined in the reaction vessel, and then one of the discrete solid supports is detected that is characterized by a temperature change in said solution greater than the temperature change of a plurality of other of said discrete solid supports in said solution. The detected solid support carries an active catalyst for the chemical reaction. Continuous flow apparatus for carrying out the method is also disclosed.

10 Claims, 8 Drawing Sheets

| FIG. 3A | FIG. 3D |
|---|---|
| FIG. 3B | FIG. 3C |

Amino Acid Monomers

METHOD AND APPARATUS FOR SCREENING CATALYST LIBRARIES

FIELD OF THE INVENTION

The present invention concerns the screening of catalyst libraries, and particularly concerns the screening of carrier-bound catalyst libraries that are produced by combinatorial chemistry techniques.

BACKGROUND OF THE INVENTION

While current understanding of chemical reactivity often makes it possible to design or choose an appropriate catalyst for a new molecular transformation, achieving adequate reactivity is often a cumbersome process. Typically, many iterations involving methodical manipulation of catalyst substructure, analysis of the resulting effect and redesign, are required. In an effort to facilitate this recursive catalyst optimization process, various research groups have started to use the techniques of combinatorial chemistry and solid phase synthesis to rapidly produce large numbers of potential catalysts. See, e.g., F. Menger et al., *J. Org. Chem.* 60, 6666 (1995); G. Liu and J. Ellman, *J. Org. Chem.* 60, 7712 (1995); K. Burgess et al., *Angew. Chem. Int. Ed. Engl.* 35, 220 (1996); B. Cole et al., *Angew. Chem. Int. Ed. Engl.* 35, 1668 (1996). Unfortunately, despite progress in evaluating the thermodynamics of equilibrium processes on solid support, methods for assessing the kinetics of reactions involving polymer-bound reagents have not been available. This circumstance has prevented the analysis of very large libraries ($10^4$–$10^6$ members) as screening for organic catalysts requires an individual assay for each member of a catalyst library.

According to the observation that most chemical reactions have a non-zero $\Delta H$, temperature has been used to survey the progress of catalytic reactions. Since all catalysts in a library assay are evaluated under the same reaction conditions, the most active catalyst will exhibit the largest temperature change ($\Delta T$~turnover frequency·$\Delta H$). Moates et al. applied this principle for the parallel evaluation of the ignition temperatures of 16 metal-doped alumina pellets in the presence of $H_2$ and $O_2$ at elevated temperatures in gas phase. F. Moates et al., *Ind. Eng. Chem. Res.* 35, 4801–4803 (1996). To date, however, there has not been a way to apply such techniques to the analysis of polymer-bound catalyst libraries for solution-phase chemical reactions.

SUMMARY OF THE INVENTION

A method for isolating an active catalyst from a library of compounds that are potential catalysts is disclosed. The method involves providing a library which comprises a plurality of discrete solid supports, each solid support having a different organic compound bound thereto (the term "organic compound" including organo-metallic compounds herein); and providing a reaction solution in a reaction vessel, the reaction solution containing the reactant or reactants necessary for a chemical reaction to occur in the presence of a catalyst for that reaction. The library and the reaction solution are then combined in the reaction vessel, and then one of the discrete solid supports is detected that is characterized by a temperature change in said solution greater than the temperature change of a plurality of other of said discrete solid supports in said solution. The detected solid support carries an active catalyst for the chemical reaction.

In a preferred embodiment of the invention, the discrete solid supports and the reaction solution are selected so that the solid supports are positioned at (for example, sink or float to) an interface in said reaction vessel. The detecting step is then carried out with an infrared detector directed at that interface. The interface may be either a gas/liquid interface (i.e., the surface of said reaction solution), or a liquid/solid interface (i.e., the bottom of said reaction vessel).

After a solid support that carries an active catalyst is detected, that solid support can be isolated and the organic compound bound thereto identified by analytical chemistry techniques or by decoding a sequential or nonsequential tag carried by that solid support.

The present invention is explained in greater detail in the drawings herein and the specification set forth below.

DETAILED DESCRIPTION OF THE INVENTION

Figure 1:
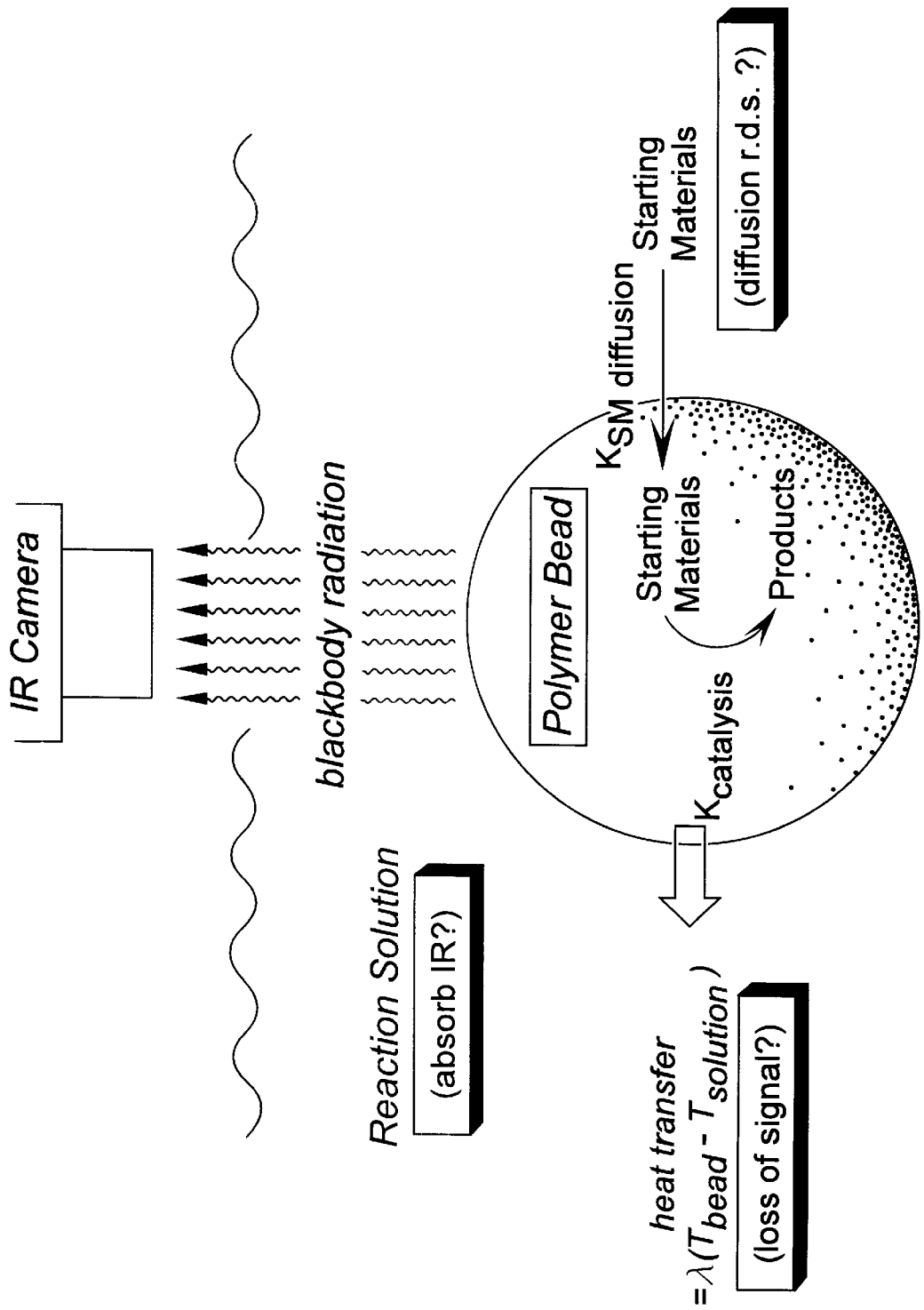
FIG. 1 schematically illustrates some of the determinants of polymer-bound catalyst detection and comparison.

The term "catalyst" herein refers to a compound that speeds the rate of a chemical reaction, but does not itself become altered by the reaction process, and is recyclable within the reaction.

Since essentially all chemical reactions involve an enthalpy change, the method described herein provides a general method for detecting catalysts for virtually any chemical reaction of interest, including both endothermic and exothermic reactions. Thus, the temperature change detected in carrying out the present invention may be either an increase in temperature or a decrease in temperature, with increases in temperature being preferred.

Libraries used to carry out the present invention are, in general, produced by any of a variety of split synthesis methods. Split synthesis methods in which a releasable tag is attached to the particle along with the organic compounds of interest are also known as cosynthesis methods. A variety of such methods are known. See, e.g., A. Furka et al., *J. Pept. Protein Res.* 37, 487 (1991); K. Lam et al., *Nature* 354, 82 (1991); R. Zuckermann et al., *Int. J. pept. Protein Res.* 40, 498 (1992); F. Sebestyen et al., *Bioorg. Med. Chem. Lett.* 3, 413 (1993); K. Lam et al., *Bioorg. Med. Chem. Lett.* 3, 419 (1993).

For example, the library may be a library of organometallic compounds wherein the compound is a metal-ligand complex. The metal in the complex may be an early or late transition metal in high, low or zero oxidation states. The metal may also be any of the main group metals, alkali metals, alkaline earths, lanthanides or actinides. The ligand in the metal-ligand complex may be composed of, or derived from, chiral or achiral forms of cyclopentadienes, amino esters, oxazolidoinones, hydroxy acids, hydroxy esters, hydroxy amides, pyridines, fused pyridines, nitrogen heterocycles, oxazoles, imidazoles, pyrroles, crown ethers, cryptands, carcerands, phosphines, diphosphines, polyphosphines, quinuclidines, quinines, alkaloids, dextrins, cyclodextrins, salens, porpyrins, biaryls, sulfonamides, Schiff bases, metallocenes, monools, diols, polyols, amines, diamines, polyamines, ammonium salts, peptides, proteins, nucleic acids, etc.

As a second example, the library may be a library of non-metal catalysts including, but not limited to, chiral or achiral forms of cyclopentadienes, amino esters, oxazolidinones, hydroxy acids, hydroxy esters, hydroxy amides, pyridines, fused pyridines, nitrogen heterocycles, oxazoles, imidazoles, pyrroles, crown ethers, cryptands, carcerands, phosphines, diphosphines, polyphosphines, quinuclidines, quinines, alkaloids, dextrins, cyclodextrins, salens, porphyrins, biaryls, sulfonamides, Schiff bases, metallocenes, monools, diols, polyols, amines, diamines, polyamines, ammonium salts, peptides, proteins, nucleic acids, etc.

As a third example, the library may be a library of ligands for ligand-accelerated metal catalysis (where the organic ligand speeds up the reaction catalyzed by the metal, which may be in the reaction solution), including but not limited to chiral or achiral forms of cyclopentadienes, amino esters, oxazolidinones, hydroxy acids, hydroxy esters, hydroxy amides, pyridines, fused pyridines, nitrogen heterocycles, oxazoles, imidazoles, pyrroles, crown ethers, cryptands, carcerands, phosphines, diphosphines, polyphosphines, quinuclidines, quinines, alkaloids, dextrins, cyclodextrins, salens, porphyrins, biaryls, sulfonamides, Schiff bases, metallocenes, monools, diols, polyols, amines, diamines, polyamines, ammonium salts, peptides, proteins, nucleic acids, etc.

The discreet solid supports may be separate from one another, or may be discreet regions on a surface portion of a unitary substrate, which surface portion may be positioned at the interface so that a plurality of the discreet regions are positioned at the interface. Such "chip-type" or "pin-type" solid supports are known. See, e.g., U.S. Pat. No. 5,288,514 to Ellman (pin-based support); U.S. Pat. No. 5,510,270 to Fodor et al. (chip-based support). Separate discreet supports (e.g., particles or beads) are currently preferred.

The discreet solid supports are formed from a polymer such as polystyrene. In general, the solid substrates are beads, which may be completely solid throughout, porous, deformable or hard. The beads will generally be at least 10 to 2000 $\mu$m, usually 20 to 500 $\mu$m, and most typically at least 50–250 $\mu$m in diameter. Any convenient composition can be used for the particles or beads, including cellulose, poreglass, silica gel, polystyrene beads such as polystyrene beads cross-linked with divinylbenzene, grafted copolymer beads such as polyethyleneglycol/polystyrene, polyacrylamide beads, latex beads, dimethylacrylamide beads, composites such as glass particles coated with a hydrophobic polymer such as cross-linked polystyrene or a fluorinated ethylene polymer to which is grafted linear polystyrene, and the like.

Synthesis of the catalyst library and linking thereof to the discreet solid support may be carried out in accordance with known techniques, such as described in U.S. Pat. No. 5,565,324 (the disclosure of which is incorporated by reference herein in its entirety), or variations thereof that will be apparent to those skilled in the art based on prior techniques and the instant disclosure.

As noted above, the discrete solid supports and the reaction solution are selected so that said solid supports migrate to an interface in said reaction vessel (See generally FIG. 1). That is, they are selected so that the solid supports either float to and position themselves at the surface of the reaction solution, or sink to and position themselves at the bottom of the reaction vessel. When sinking solid supports are employed, the bottom of the reaction vessel should be formed from a material that is transparent to the temperature sensing device. For example, where an infrared detector such as an infrared camera is employed, the bottom of the reaction vessel may be formed from quartz or sapphire. The detecting step is then carried out by directing the temperature detector to the desired interface: where the supports position themselves at the surface of the reaction solution, the temperature detector is positioned above and directed to the surface of the reaction solution; where the supports position themselves at the bottom of the reaction vessel, the temperature detector is positioned below and directed at the exterior of the bottom portion of the reaction vessel.

The term "adjacent" as used herein means that the solid supports are in such close proximity to the interface (e.g., reaction solution—air interface; reaction solution—window interface) that the temperature thereof may be detected by an infra-red detector positioned outside of the reaction solution and directed at the interface. The solid supports may contact or reside at the interface, or slightly below or separated from the interface, but within about 300 or 500 $\mu$m of the interface (depending on the choice of solvent, flow conditions, etc.). If a volume of reaction solution is interposed between the solid support and the interface, it must be sufficiently small that that volume of reaction solution will be heated or cooled by the solid support, and detectable by the infra-red detector, or sufficiently small so that it does not block the infra-red signal from the solid support.

The temperature change may be detected by any suitable temperature sensing or detecting device, such as an infrared detector or an infrared camera. Other temperature detecting means are discussed in greater detail below.

Temperature change may also be detetected indirectly, by employing solid supports constructed of a material that changes color in response to a change in temperature, and then detecting a color change in the bead or particle. Color change may be detected by any suitable means, including by detecting a change in light transmission through the particle.

The solid support that is detected in the manner described above may be detected and isolated by any suitable technique, including manually or automatically. A continuous flow process for isolating the solid support is described in connection with FIG. 5 below. Where batches of beads are employed and examined with an infra-red camera, a device for removing specific beads may be conveniently constructed by inserting a needle into the eraser of a pencil and using the eye of the needle as a spoon to lift out specific beads.

The organic compound carried by the isolated solid support may be identified by any suitable technique or combination of techniques, as will be apparent to those skilled in the art, including, but not limited to, deconvolution and indexed combinatorial chemistry. If desired, each solid support may carry a tag such as a tag molecule that serves to uniquely identify the compound carried by that solid support. Such tag molecules may be sequential tags, including but not limited to oligonucleotide tags and oligopeptide tags. See, e.g., S. Brenner and R. Lerner, *Proc. Natl. Acad. Sci. USA* 89, 5381 (1992); J. Kerr et al., *J. Am. Chem. Soc.* 115, 2529 (1993). Such tag molecules may also be nonsequential tags, such as described in U.S. Pat. No. 5,565,324 to W. Clark Still et al. (the disclosure of which is incorporated by reference herein in its entirety). Where tag molecules are employed, the organic compound may be identified by decoding the tag in accordance with known techniques, rather than by determining the structure of the organic compound itself. Any tag technique can be used, including radio frequency tags. See, e.g., Nicolau et al., *Angew Chem. Int. Ed. Engl.* 34, 2289 (1995).

The reaction solution is, in general, a liquid, and preferably comprises a halogenated organic solvent, such as chloroform or methylene chloride. The reactant or reactants contained within the reaction solution depend upon the particular reaction involved.

Figure 5:
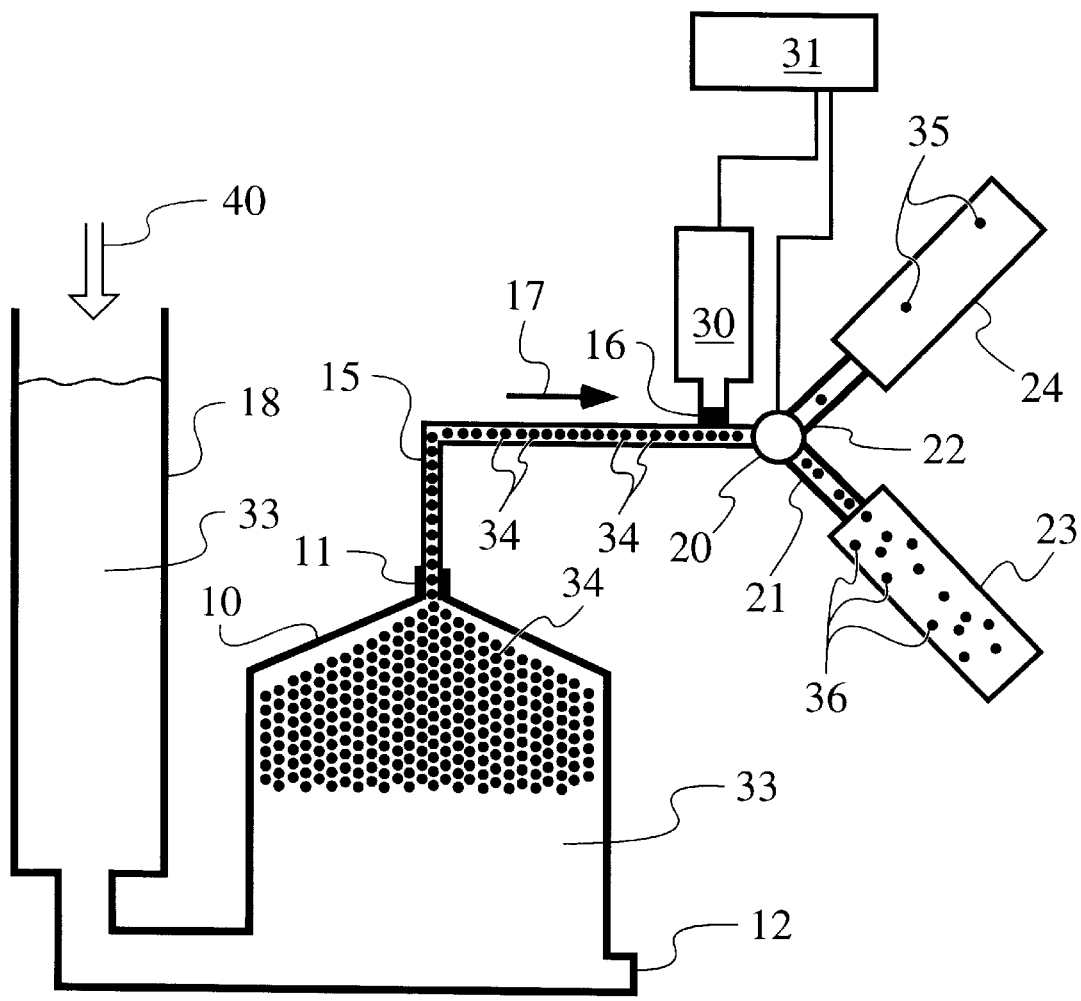
FIG. 5 is a schematic illustration of an apparatus used to carry out the present invention.

An apparatus that may be used to carry out the method of the present invention is schematically illustrated in FIG. 5. In general, the apparatus comprises a chamber 10 for carrying the discreet solid supports, the chamber having an upper outlet opening 11 and a lower outlet opening 12 (the lower outlet opening being closed in the illustrated embodiment). The upper outlet opening is employed with the density of the solvent is greater than the density of the solid supports; the lower outlet opening is employed with the density of the solvent is less than the density of the solid supports. As will be appreciated based on the present disclosure, many of the elements and techniques used in cell sorting apparatus may be used in carrying out the present invention. See generally M. Melamed et al., *An Historical Review of the Development of Flow Cytometers and Sorters*, pgs 1–9 in Flow Cytometry and Sorting (2d Ed. 1990 Wiley-Liss, Inc.).

A flow tube 15 is connected to the chamber, the flow tube having a window 16 positioned in the side wall thereof at at a location by which said discreet solid supports must pass (direction of flow of the solid supports in the reaction solution being indicated by arrow 17). Where the term "reaction vessel" is employed herein, the flow tube is considered to be a part of the reaction vessel. The window is in a preferred embodiment transparent to infra-red energy, and is formed of a material such as quartz or sapphire. It will be appreciated that the window may be formed from a separate piece of material than the tube, or that the entire tube, or a segment of the tube, may be formed from a material suitable for use as a window. A reserve reservoir 18 is connected to the chamber to provide a source of positive pressure (indicated by arrow 40) to the reaction solution so that the beads are caused to flow through the flow tube in the direction indicated by arrow 17.

A flow deflector 20 is connected to the flow tube at a position downstream from the window, the flow deflector having first and second outlet openings 21, 22. Collection reservoirs 23, 24 are in fluid communication with each of the outlet openings. Any suitable flow deflector can be used, including pneumatic, hydraulic, or electrostatic flow deflectors as employed in cell sorters and the like. See, e.g., U.S. Pat. No. 3,560,754 (the disclosure of all patent references are incorporated herein by reference).

An infra-red detector 30 serves as a temperature detection means and is operatively associated with the window; and a controller 31 is operatively associated with both the infra-red detector and the flow deflector. Other temperature detection means may also be employed. For example, where solid supports that change color in response to a change in temperature are employed, an optical microscope, a light detector, an ultraviolet light detector, a refractive index detector, a thermocouple or the like may be used in place of the infra-red detector. A source of illumination may be provided in operative association with the temperature detection device and the transmission of light through the solid support detected to determine temperature change. Where a thermocouple is employed, the need for a window may be obviated, so long as the solid supports flow past the thermocouple in sufficient proximity thereto for temperature of each discreet support to be separately detected.

The controller, which is typically a microprocessor controller, is programmed or configured to cause the flow deflector to deflect the discreet solid supports through either said first or second outlet opening based on the temperature of the solid support detected by the infra-red detector, as explained in greater detail below.

The flow tube 15, or at least at the portion thereof operatively associated with the temperature detection means and incorporating the window 16, forms a constricted channel or aperture through which the solid supports must pass in an essentially single-file, or columnar, pattern. The diameter of the flow tube at this point will depend upon the diameter of the solid supports themselves, the choice of temperature detection means, the flow conditions, etc. In general, where an infra-red detector serves as the temperature detection means, the flow tube should be configured so that the solid supports are positioned adjacent the window as they flow by the window. This can be achieved by employing a narrow flow tube (e.g., one having an internal diameter not greater than two or three times that of the solid support). Narrower tubes are preferred at higher rates of flow. If larger diameter tubes are desired (for example, to reduce potential blockage) then a modified version of a sheath-flow technique may be employed, with the reaction solution carrying the solid supports injected into the laminar flow sheath liquid in an offset rather than concentric pattern, so that the reaction solution and the supports flow along a path that is adjacent the window. The sheath flow liquid may be the same as or different from the reaction solution. The sheath flow liquid may be selected to have a greater viscosity than the reaction solution to help contain the flow of the reaction solution along the desired path adjacent the window. In addition, if desired, the sheath-flow liquid may be selected to be immiscible with the reaction solution to assist in containing the flow of the reaction solution along the desired path. If temperature is detected by other means, such as a color change of the solid support, then it is not necessary to position the solid support adjacent the window and conventional sheath flow techniques may be employed.

In the use of an apparatus of FIG. 5, the reservoir and chamber contain a reaction solution 33 and solid supports 34. The solid supports are caused to pass through the flow tube, past the window, while remaining in the reaction solution. The flow tube and the window are configured so that the solid supports are positioned adjacent the interface formed between the reaction solution and the window as the solid supports flow past the window. The temperature of the solid supports is detected as they pass the window to identify solid supports that are characterized by a temperature change in the solution greater than (that is, different from) the temperature change of a plurality of other of said solid supports. Those solid supports that are characterized by such a temperature change 35 are then separated from those that are not with the flow deflector; those solid supports that are characterized by such a temperature change carry an active catalyst for the chemical reaction. As above, when the chemical reaction is an exothermic reaction, the temperature change is an increase in temperature; when the chemical reaction is an endothermic reaction, the temperature change is a decrease in temperature.

In the Examples set forth below, "DMAP" means dimethylaminopyridine, "IR" means infrared, "GLC" means gas liquid chromatography, "g" means grams, "mg" means milligrams, "mL" means milliliters, "mmol" means millimoles, and temperatures are given in degrees Centigrade unless otherwise indicated.

EXAMPLE 1

Catalytic Acylation of Ethanol with Polymer Beads

The catalytic acylation of ethanol with acetic anhydride was chosen as a test system for methods development. Since the reaction is relatively exothermic and is catalyzed by a simple non-metal catalyst (DMAP) with exceptional turnover rates, this system proved to be optimal for initial study. Preliminary experiments were carried out on 300 micron TENTAGEL™ macrobeads (0.33 mmol/g, Rapp Polymere) and involved addition of ~3 mg of various catalyst beads to 1.1 mL of 8:1:1:1 chloroform:ethanol:acetic anydride:triethyl amine. As depicted in Table 1, significant temperature increases can be achieved with polymer-bound catalysts. For instance, whereas addition of acylated polymer beads (1, no catalyst) to the reaction solution results in only a small temperature increase (+0.1° C.) as measured by a thermocouple, addition of 3 mg of a polymer-bound version of DMAP (3, prepared by coupling N-4-pyridylproline (prepared by palladium-catalyzed arylation of 4 brompyridine with L-proline tert-butyl ester as described in S. Wagaw et al., *J. Org. Chem.* 61, 7240 (1996)) to 300 micron TENTAGELT™ S-$NH_2$, 1.04 mmol/g, Rapp Polymere) results in a brief 3.4° C. temperature increase of the bulk reaction solution. Addition of beads derived from a less active pyridine nucleus (2), results in a temperature increase of only 2.0° C., indicating that diffusion of starting material through the polymer matrix does not necessarily liimit the reaction rate and preclude catalyst comparison.

TABLE 1

Increase in Reaction Temperature Resulting from Addition of Polymer-Bound Catalyst Beads*.

$$EtOH + Me\text{-}CO\text{-}O\text{-}CO\text{-}Me \xrightarrow[\text{CHCl}_3]{\text{Catalyst, TEA}} EtO\text{-}CO\text{-}Me + HO\text{-}CO\text{-}Me$$

| Compound | Structure | Reaction Initial | Temperature Maximum | (° C.) ΔT |
|---|---|---|---|---|
| 1 | 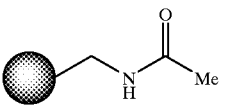 | 22.6 | 22.7 | 0.1 |
| 2 | 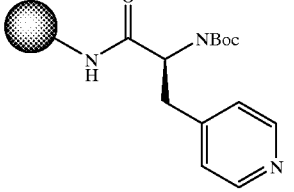 | 20.7 | 22.7 | 0.1 |
| 3 | 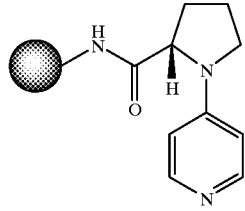 | 22.5 | 25.9 | 3.4 |

*Conditions: 3.0 mg of catalyst beads (prepared on 300 micron tentagel S-$NH_2$ macrobeads, 0.33 mmol/g, Rapp Polymere) were added to a stirred solution of 1.1 mL of 8:1:1:1 $CHCl_3$:TEA:EtOH:$Ac_2O$. The reaction temperature was measured by a thermocouple, and the initial and maximum temperature achieved were recorded.

EXAMPLE 2

Use of Infrared Camera to Detect Temperature Change

As a next step, an infrared camera (Cincinnati Electronics IRRIS 256ST, 256×256 InSb FPA detector) was used to compare the temperature of individual beads both with and without catalyst attached. The camera was positioned over the reaction vessel and directed towards to the surface of the solvent. Whereas, in the reaction solution used in Example 1 above, it is not possible to see individual non-catalyst beads 1 (bead temperature rapidly equilibrates with solvent), when catalyst beads 3 are added to the reaction solution they exhibit a sustained ~1° C. temperature increase from that of the bulk solvent. This temperature difference is easy to observe with the IR camera (data not shown) indicating that active catalyst beads can be reliably distinguished from inactive catalyst beads. Importantly, with chloroform as solvent, the beads float on top of the reaction solution thus avoiding solvent interference with IR transmission. When the proportion of chloroform is reduced such that the beads sink, it is not possible to observe hot beads with the camera.

EXAMPLE 3

Trimeric Library of Potential Catalysts

Figure 2:
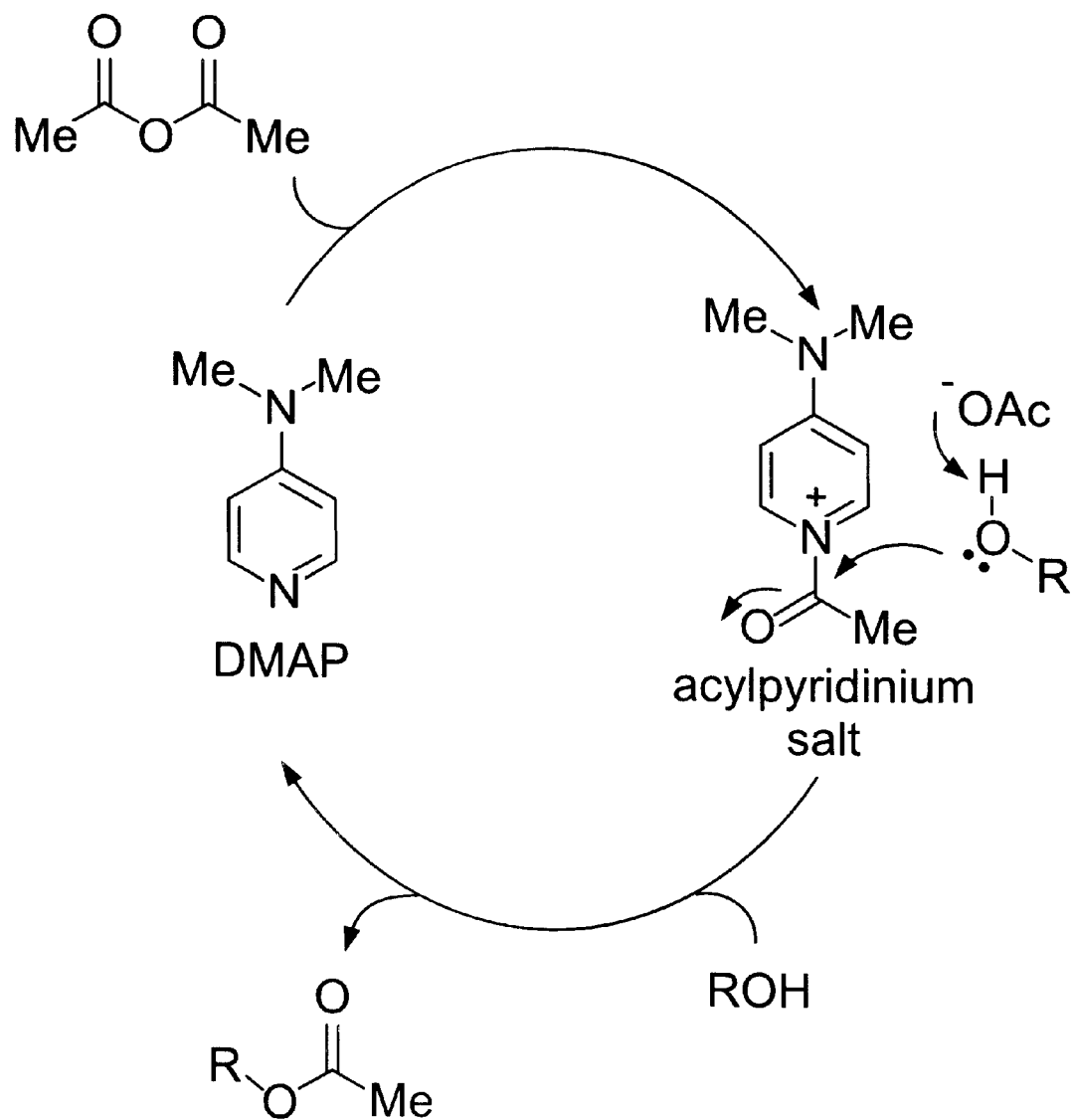
FIG. 2 illustrates the mechanism for the DMAP catalyzed reaction between acetic anhydride and alcohols.
Figures 3, 3A:
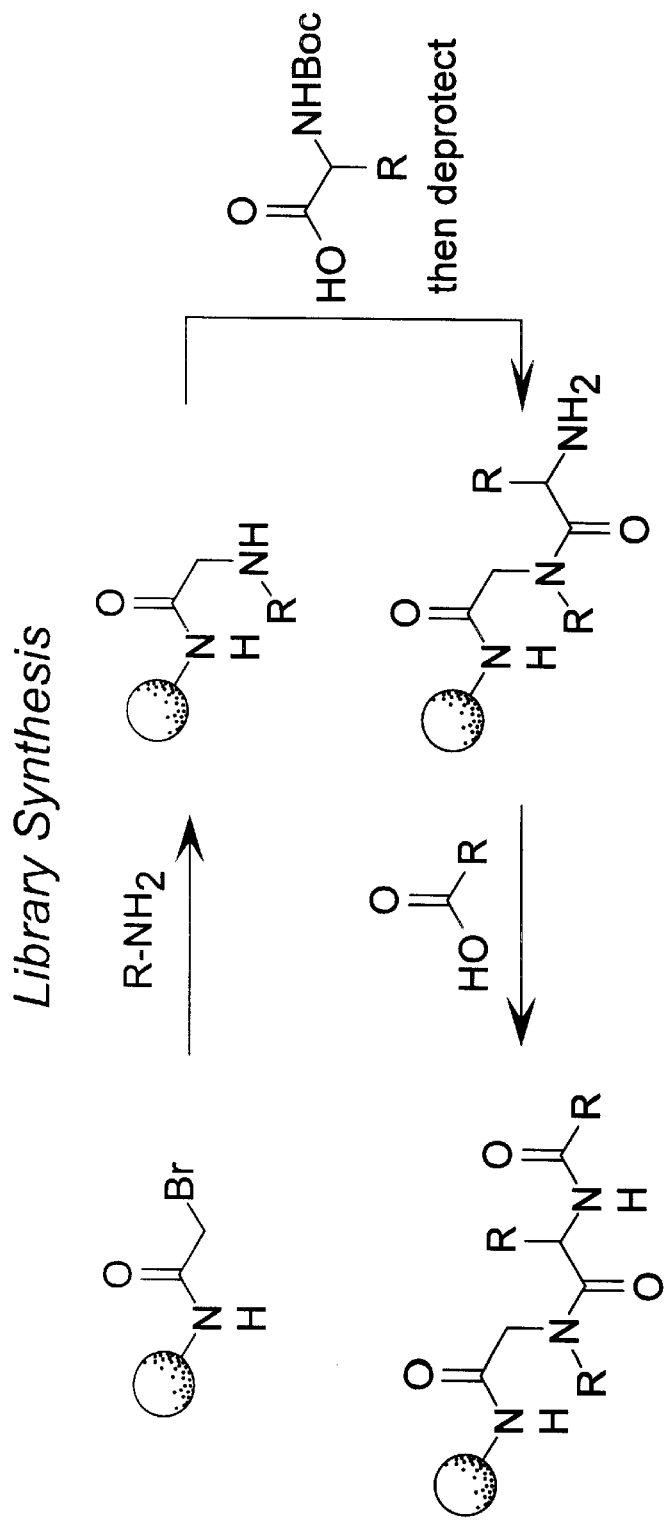
FIG. 3 illustrates the synthesis scheme and monomers used in the three positions of the trimeric catalyst library.
Figure 3B:
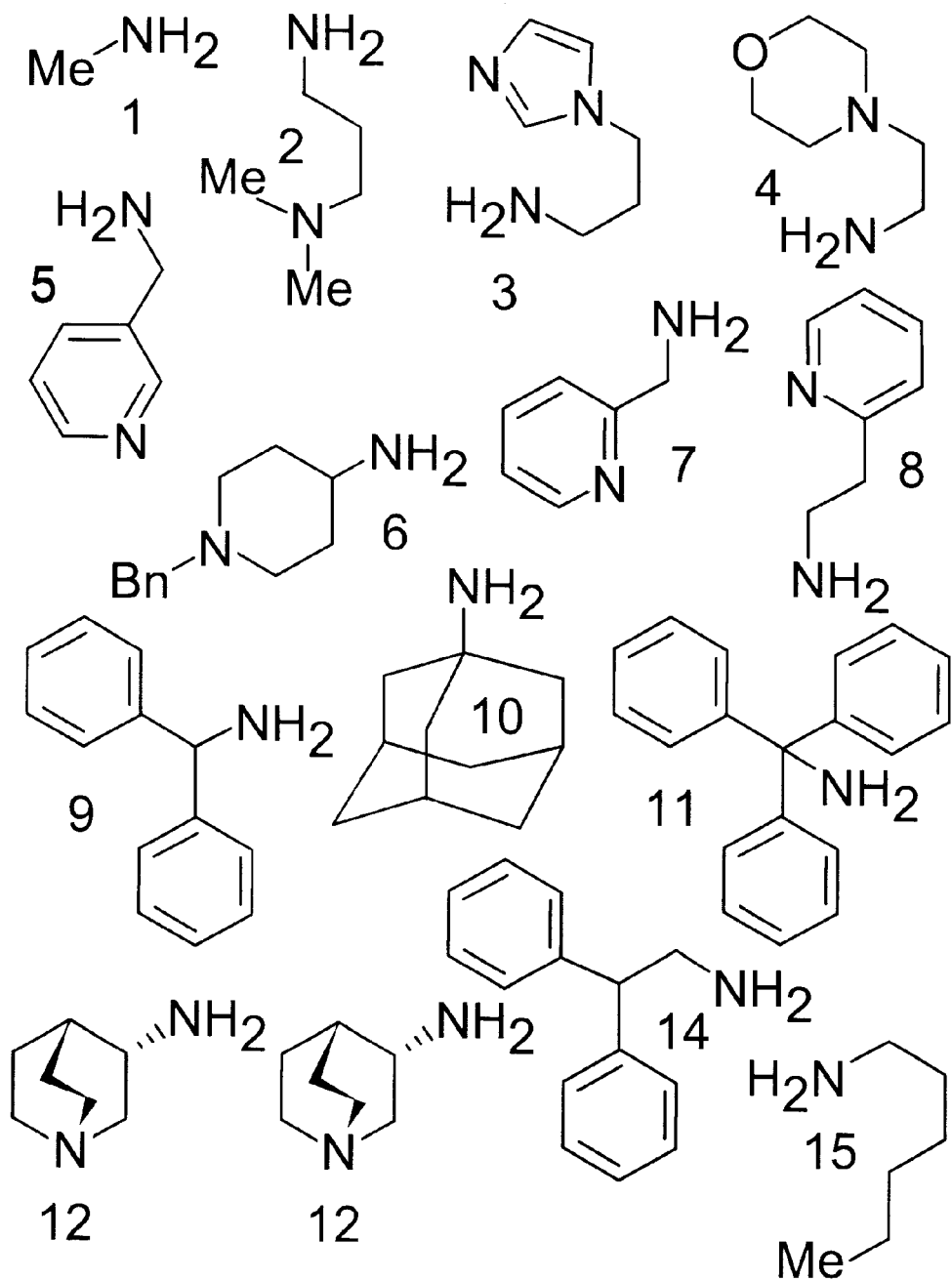
Figure 3C:
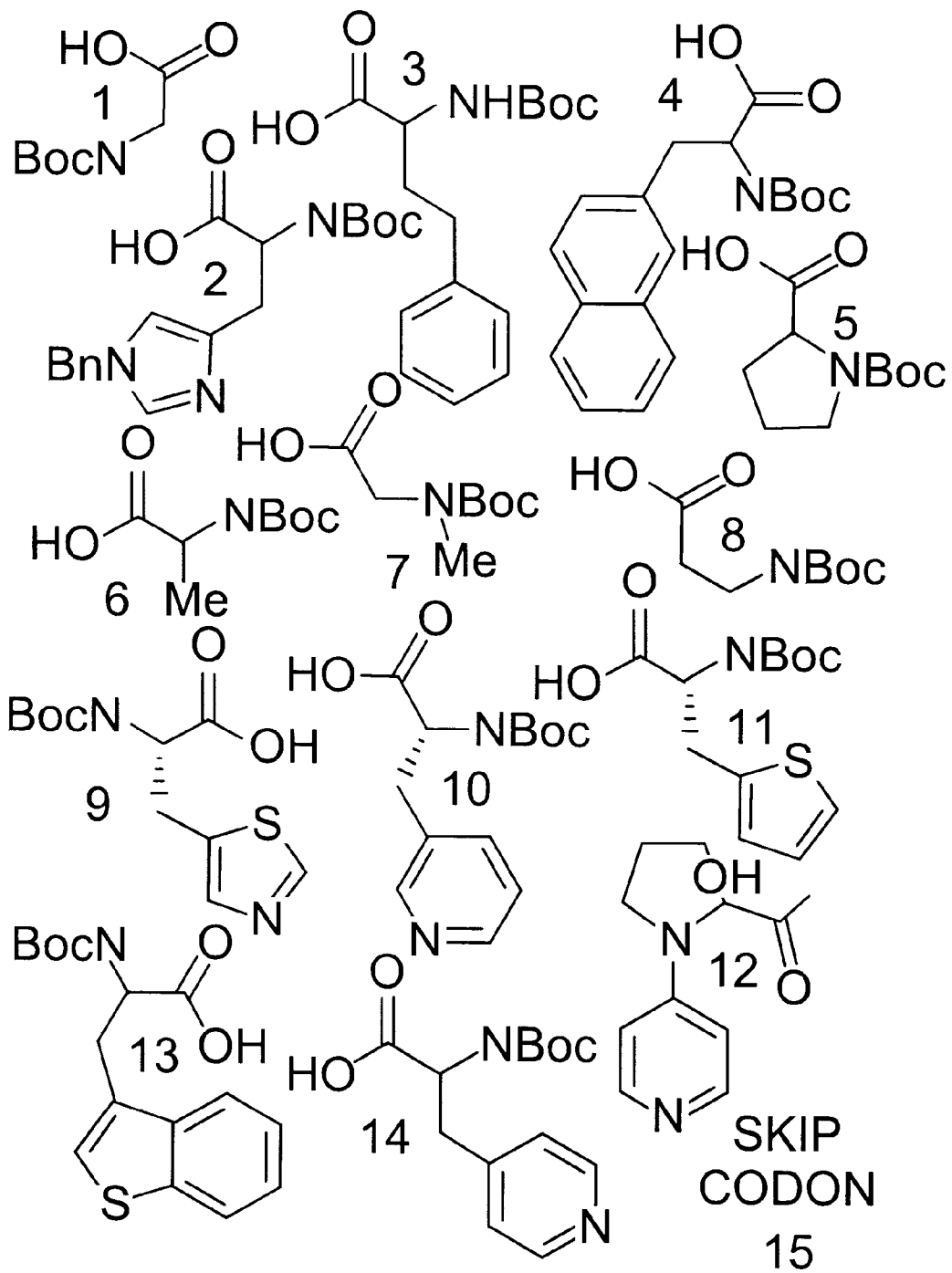
Figure 3D:
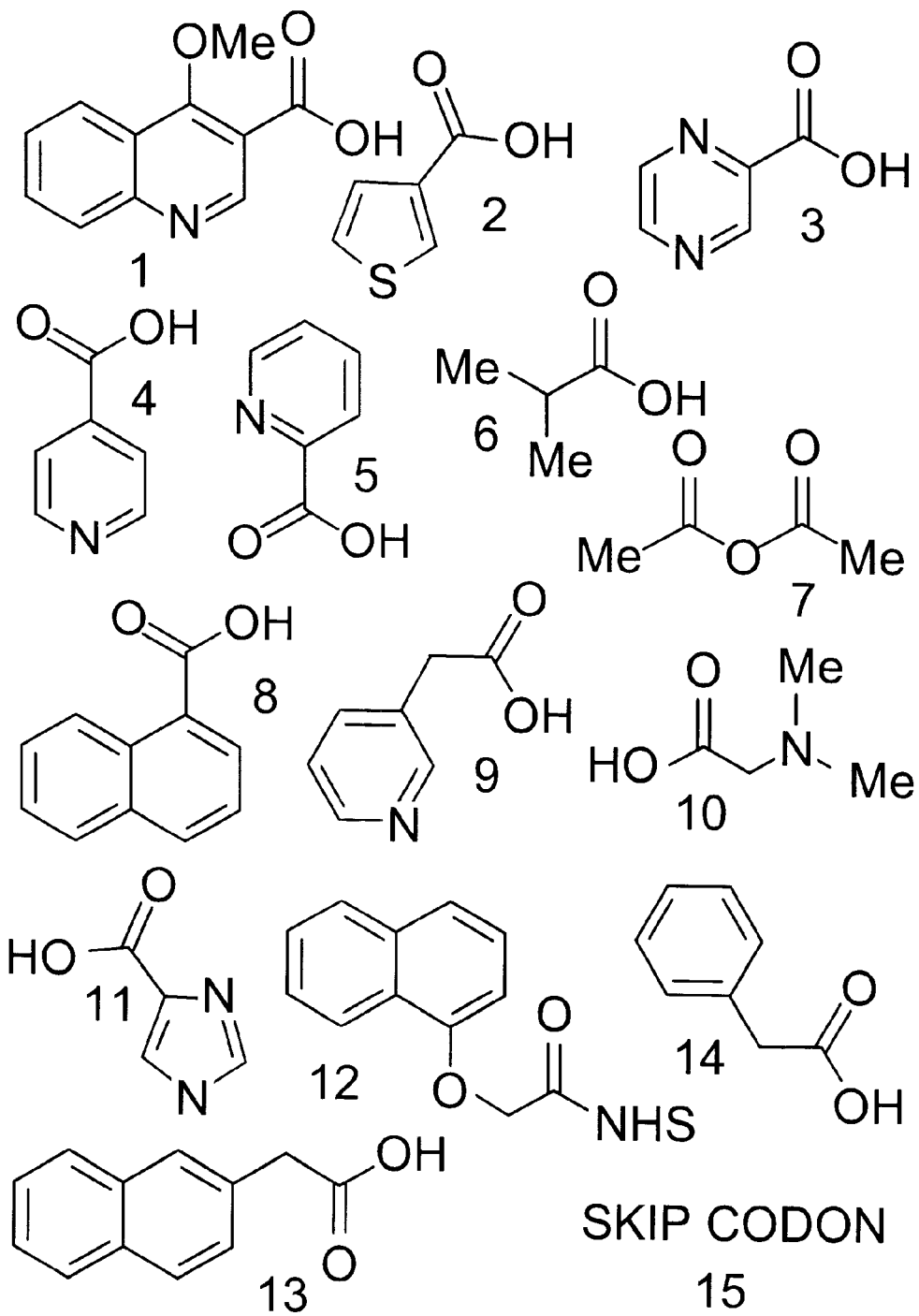

A trimeric library of potential catalysts for the acylation reaction was prepared. It was envisioned that, based on the known mechanism for pyridine catalyzed acylation of alcohols (see FIG. 2), a suitable base covalently tethered in the correct orientation relative to the nucleophilic center might increase catalyst activity through a bifunctional catalytic manifold. In this regard, the internal base might act to deprotonate the reacting alcohol, in an intramolecular fashion, as it adds to the acylpyridinium salt derived from the catalyst. This would be reminiscent of the manner in which the liberated acetate deprotonates the reacting alcohol in DMAP catalysis (FIG. 3). Accordingly, an encoded (M. Ohlmeyer et al., *Proc. Natl. Acad. Sci. USA* 90, 10922 (1993)) library was prepared by split/pool solid phase synthesis (A. Furka et al., *Intl. J. Pept. Protein Res.* 37, 487 (1991)) using the reaction sequence and monomers shown in FIG. 3. As well as incorporating a variety of basic groups and a diverse collection of potentially nucleophilic compounds, a subset of library monomers were chosen at random in the chance that they might act through an unpredicted mode of catalysis. For library synthesis, initial displacement of an activated bromide with a variety of primary amines was followed by coupling a variety of protected amino acids to the resulting secondary amine nitrogen. After deprotection, a collection of carboxylic acids were coupled to the liberated amine terminus thus completing the trimeric library. With 15 monomers in each position (including a skip codon) (A. Combs et al., *J. Am. Chem. Soc.* 188, 287 (1996)), the library should be composed of 3375 distinct compounds. Library synthesis was performed on aminomethyl polystyrene macrobeads (500 micron, 1.04 mmol/g, Rapp Polymere) as these were found to give the largest temperature increase (+16° C./3 mg) in the thermocouple assay described earlier.

Addition of 610 mg of library resin beads (~7000 beads) to a solution composed of 40 mL chloroform, 6 mL ethanol, 6 mL triethyl amine and 3 mL acetic anhydride was followed by isolation of beads determined to be hot as viewed by the infrared camera (not shown). Subsequent decoding of isolated beads revealed the sequences shown in Table 2. Out of the 23 selected and decoded hot beads, 21 were either (S,S)-4 or (R,S)-4, prepared from amines 12 and 13, coupled to acid N-4-pyridylproline. It should be noted that attachment of monomer 12 in the amino acid position effectively terminates compound synthesis since 12 does not have an amine on which to couple an acid in the third position. In addition to the diastereomers of 4, hot beads containing sequences coding for compounds 5 and 6 were also recovered.

TABLE 2

Selection Frequency and structures of beads from the infrared catalyst library assay.

| Compounds | Structure | occurrences | encoding sequence | | |
|---|---|---|---|---|---|
| | | | amine | amino acid | acid |
| (S,S)-4 | [structure] | 11 | 12 | 12 | — |
| (R,S)-4 | [structure] | 10 | 13 | 12 | — |

TABLE 2-continued

Selection Frequency and structures of beads from the infrared catalyst library assay.

| Compounds | Structure | occurrences | encoding sequence amine | amino acid | acid |
|---|---|---|---|---|---|
| 5 | [structure] | 1 | 5 | 12 | — |
| 6 | [structure] | 1 | 1 | 5 | 4 |
| 7 | [structure] | 0 | 14 | 12 | — |

EXAMPLE 4

Kinetic Experiments

Figure 4:
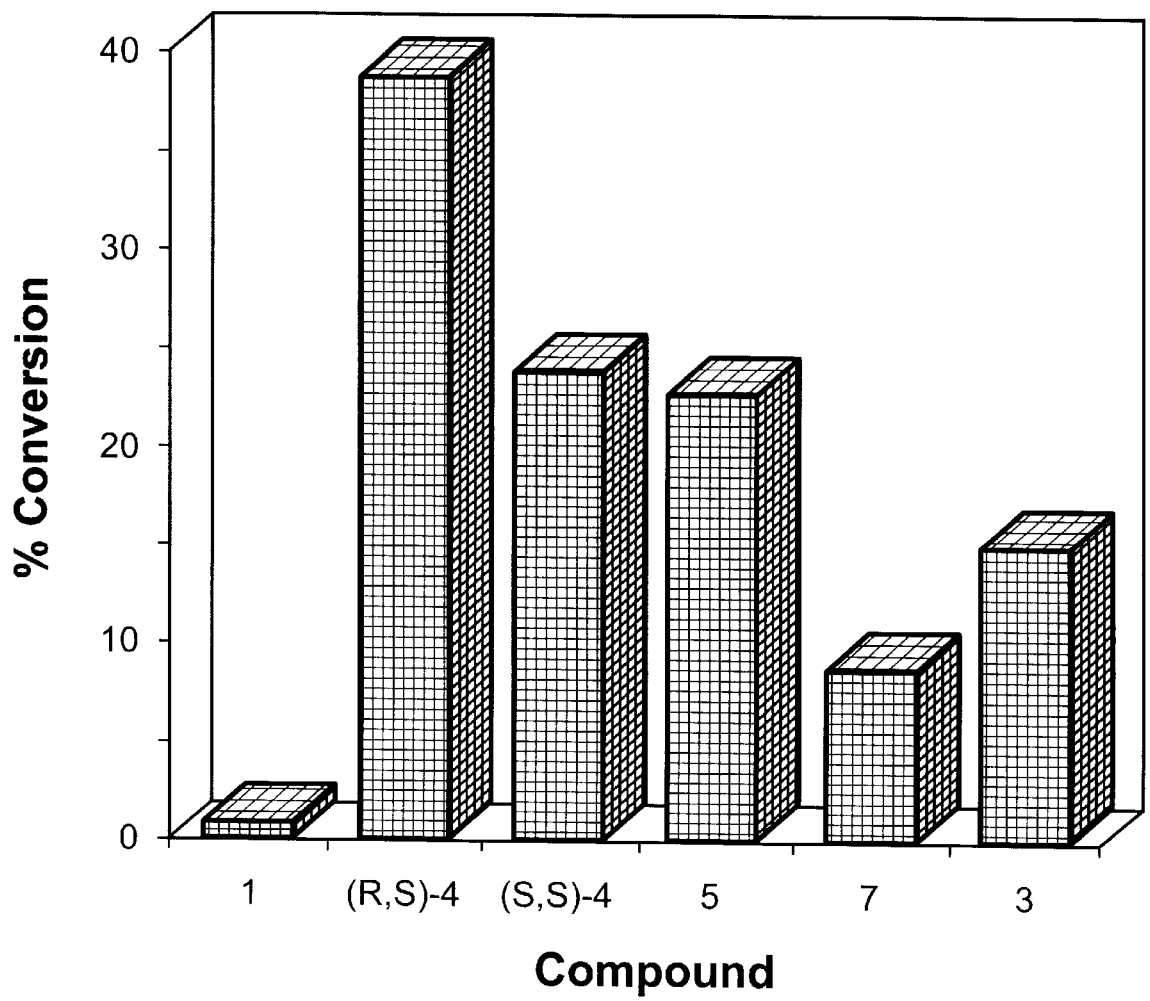
FIG. 4 illustrates conversion above background (13.3%) at 9 minutes for selected polymer bead-bound compounds. Conditions: 5 beads (500 micron polystyrene, 1.04 mmol/g) of a given compound were added to a stirred solution of 1.1 mL of 8:1:1:1 chloroform:triethyl amine:ethanol:acetic anhydride. conversion was measured versus to aliquot.

The strong consensus sequence observed in selected beads in Example 3 above highlights the reproducibility of the infrared library assay. In order to ascertain whether the assay truly reflects catalyst activity and not unappreciated effects, catalysts of interest were studied with a series of kinetic experiments. After resynthesis on aminomethyl polystyrene, five beads of a given catalyst were added to 1.1 mL of an 8:1:1:1 solution of chloroform:acetic anhydride:ethanol:triethyl amine containing 20 µL of toluene as an internal standard. Aliquots (1 µL) were taken at to and at nine minutes and immediately subjected to GLC analysis. Conversion was measured by comparing the amount of remaining acetic anhydride (versus the internal standard) to the amount at $t_0$. FIG. 4 shows the average data from three kinetic runs for each type of polymer bound catalyst. After subtraction of background reaction (13% at nine minutes), non-catalyst beads (1) showed little catalytic activity (~5% conversion after 9 minutes). Catalyst beads (3), which were not present in the library, showed ~15% conversion and beads composed of structure 7, a catalyst that should have been present in the library but was not selected, afforded 10% conversion. Hot beads (R,S)-4, (S,S)-4 and 5, all gave significantly higher conversions (38%, 24% and 23%, respectively) as compared to both the non-selected beads and the DMAP beads. Of note, is that the most strongly selected beads, (R,S)-4 and (S,S)-4, also showed more efficient catalysis in the kinetic runs as compared to the singly selected bead 5, indicating that the infrared assay can discriminate between varying levels of catalyst activity. While simply comparing conversion may lead to the conclusion that (R,S)-4 is only about twice as active as 3 (38% versus 15% conversion), there is likely a much larger difference. With background reaction included, ~52% conversion has been reached with (R,S)-4 meaning that limited remaining starting material has likely slowed the reaction significantly as compared to the initial rate of reaction. While this effect will occur with 3 as well, at 28% conversion (including background reaction) it is at a much smaller extent.

The foregoing is illustrative of the present invention, and not to be construed as limiting thereof. The invention is defined by the following claims, with equivalents of the claims to be included therein.

That which is claimed is:

1. A method for isolating an active catalyst from a library of compounds that are potential catalysts, said method comprising:

providing a library which comprises a plurality of discrete solid supports, each solid support having a different organic compound bound thereto;

providing a reaction solution in a reaction vessel, said reaction solution containing the reactant or reactants necessary for a chemical reaction to occur in the presence of a catalyst for said reaction, wherein said reaction solution is a liquid;

combining said library with said reaction solution in said reaction vessel, wherein said discrete solid supports are positioned at an interface in said reaction vessel; and then detecting one of said discrete solid supports characterized by a temperature change of said one discrete solid support in said solution greater than the temperature change of a plurality of other of said discrete solid supports in said solution, said detected solid support carrying an active catalyst for said chemical reaction;

wherein said detecting step is carried out with an infrared detector, with said infrared detector directed at said interface, and with said infrared detector positioned outside of said reaction solution and directed at the interface;

and wherein said discrete solid supports and said reaction solution are selected so that said discrete solid supports float in said reaction solution, and said infrared detector is positioned above and directed at the surface of said reaction solution.

2. A method according to claim 1, wherein said temperature change is an increase in temperature.

3. A method according to claim 1, wherein said temperature change is a decrease in temperature.

4. A method according to claim 1, further comprising the steps of:

isolating said detected solid support; and then identifying the organic compound bound to said detected solid support.

5. A method according to claim 4, wherein each of said solid supports carries a different sequential tag, and wherein said identifying step is carried out by decoding said sequential tag.

6. A method according to claim 4, wherein each of said solid supports carries a different nonsequential tag, and wherein said identifying step is carried out by decoding said nonsequential tag.

7. A method according to claim 1, wherein said reaction solution comprises a halogenated organic solvent.

8. A method according to claim 7, wherein said halogenated organic solvent is selected from the group consisting of chloroform and methylene chloride.

9. A method according to claim 1, wherein said discrete solid supports are polymer beads.

10. A method according to claim 9, wherein said polymer beads are polystyrene beads.

* * * * *